United States Patent
Fukuda et al.

[11] Patent Number: 6,080,859
[45] Date of Patent: Jun. 27, 2000

[54] PYRROLOINDOLE DERIVATIVES AND INTERMEDIATES IN PRODUCING THE SAME

[75] Inventors: Yasumichi Fukuda, Tochigi; Rumiko Shimazawa, Tokyo; Yasuo Oomori, Tokyo; Shiro Terashima, Tokyo, all of Japan

[73] Assignee: Kyorin Pharmaceutical Co., Ltd., Tokyo, Japan

[21] Appl. No.: 09/341,872

[22] PCT Filed: Jan. 22, 1998

[86] PCT No.: PCT/JP98/00234

§ 371 Date: Jul. 19, 1999

§ 102(e) Date: Jul. 19, 1999

[87] PCT Pub. No.: WO98/32757

PCT Pub. Date: Jul. 30, 1998

[30] Foreign Application Priority Data

Jan. 24, 1997 [JP] Japan ..................... 9-011289

[51] Int. Cl.[7] ..................... A61K 31/5377; C07D 413/14
[52] U.S. Cl. ..................... 544/143; 544/69; 544/142; 544/373; 546/199; 548/433; 514/235.2
[58] Field of Search ..................... 544/143; 546/199; 548/433

[56] References Cited

U.S. PATENT DOCUMENTS 5,629,430   5/1997   Terashima et al. ..................... 548/421

FOREIGN PATENT DOCUMENTS 3-240779  10/1991   Japan .
5-51384    3/1993   Japan .
5-97853    4/1993   Japan .

*Primary Examiner*—Robert W. Ramsuer
*Attorney, Agent, or Firm*—McAulay Nissen Goldberg Kiel & Hand, LLP

[57] ABSTRACT

Pyrroloindole derivatives having antimicrobial and antitumor activities and having a carbamoyloxy group represented by the following general formula (1), optical isomers thereof, and pharmacologically acceptable salts thereof; and intermediates for production thereof:

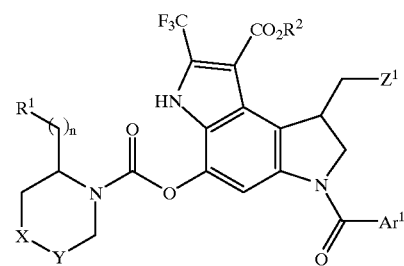

(1)

where $R^1$ is OH, or a pyrrolidinyl group; n is 1 or 2; $R^2$ is a lower alkyl group of $C_1-C_4$; X—Y or Y—X is $CH_2$, CHOH, $CH_2$-$CH_2$, O—$CH_2$, or NMe—$CH_2$; $Z^1$ is Cl or Br; and $Ar^1$ is a.

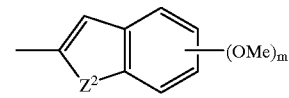

b.

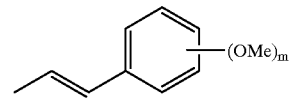

c.

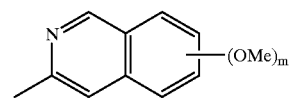

d.

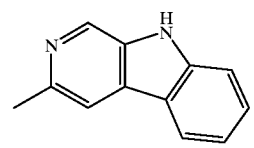

e.

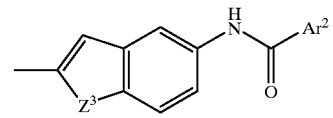

wherein $Z^2$ and $Z^3$ are O or NH; m is 0 or an integer of 1 to 4; and $Ar^2$ is any of the above groups a, b, c, and d.

7 Claims, No Drawings

PYRROLOINDOLE DERIVATIVES AND INTERMEDIATES IN PRODUCING THE SAME

TECHNICAL FIELD

The present invention relates to novel pyrroloindole derivatives having a carbamoyloxy group which have antimicrobial and antitumor activities, optical isomers thereof, and pharmacologically acceptable salts thereof; and intermediates for production thereof.

BACKGROUND ART

CC-1065, which is an antibiotic having antimicrobial activity and antitumor activity, is disclosed in J.Antibiotics, vol.31, p.1211 (1978), and vol.34, p.1119 (1981); and U.S. Pat. No. 4,169,888. Duocarmycin A having analogous structure, and analogues thereof are disclosed in WO87/06265; EP0318056; J.Antibiotics, vol.42, p.1229 (1989); and JP-A-4-99774. Derivatives of CC-1065 are disclosed in EP0359454, JP-A-60-193989, and published Japanese translation of PCT application (Kohyo) 2-502005. Derivatives of duocarmycins are disclosed in JP-A-3-7287, JP-A-3-128379, EP0354583, and EP0406749. These are derived by utilizing directly a basic skeleton of a natural substance, or modification of a natural product. Further, a chemically synthesized pyrroloindole derivative having a trifluoromethyl group on the pyrroloindole ring is disclosed by the inventors of the present invention in JP-A-6-116269.

The inventors of the present invention made comprehensive researches on pyrroloindole derivatives which are effective against solid tumor and is less toxic. Consequently, The inventors found a derivative having a trifluoromethyl group in the pyrroloindole ring, and disclosed it in JP-A-6-116269. In JP-A-6-116269, a prodrug represented by Formula A having a carbamoyl group containing a cyclic amine is disclosed.

A

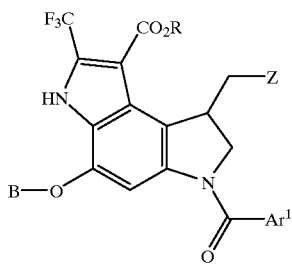

B: MeN NCO, HOCH$_2$CH$_2$N NCO, etc.

The present invention intends to provide a prodrug which forms an active species (a compound of Formula A in which B is hydrogen) in vivo more readily than the prodrug shown in Examples of JP-A-6-116269, and is effective against solid tumor and is less toxic.

DISCLOSURE OF INVENTION

It was found by the inventors of the present invention that the pyrroloindole derivatives having a carbamoyloxy group represented by the following general formula (1) below, optically active isomers thereof, and pharmacologically acceptable salts thereof are useful as the aforementioned prodrug.

(1)

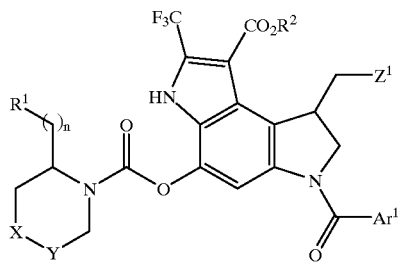

where $R^1$ is OH, or a pyrrolidinyl group; n is 1 or 2; $R^2$ is a lower alkyl group of $C_1$–$C_4$; X—Y or Y—X is $CH_2$, CHOH, $CH_2$–$CH_2$, O—$CH_2$, or NMe—$CH_2$; $Z^1$ is Cl or Br; and $Ar^1$ is a.

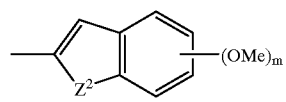

(wherein $Z^2$ is O or NH, m is 0 or an integer of 1 to 4), b.

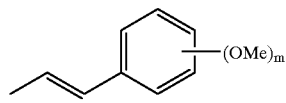

(wherein m is 0 or an integer of 1 to 4), c.

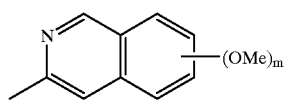

(wherein m is 0 or an integer of 1 to 4), d.

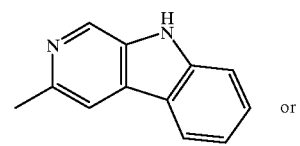

or e.

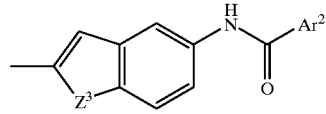

(wherein $Z^3$ is O or NH; $Ar^2$ is any of the above groups a, b, c, and d). Consequently the present invention has been completed.

The present invention further relates to protected pyrroloindole derivatives represented by the following general formula (2):

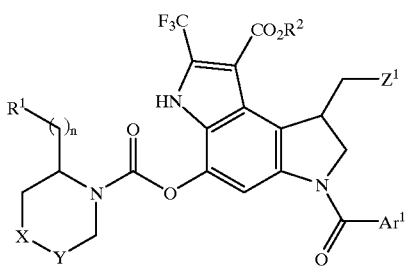

(2)

where $R^1$ is $OR^3$ ($R^3$ is a protecting group for the hydroxyl group); n is 1 or 2; $R^2$ is a lower alkyl of $C_1$–$C_4$; X—Y is $CH_2$, CHOH, $CH_2$—$CH_2$, O—$CH_2$, or NMe—$CH_2$; $Z^1$ is Cl or Br; and $Ar^1$ is a.

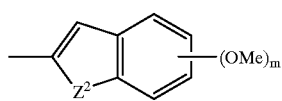

(wherein $Z^2$ is O or NH, m is 0 or an integer of 1 to 4), b.

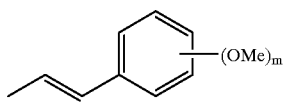

(wherein m is 0 or an integer of 1 to 4), c.

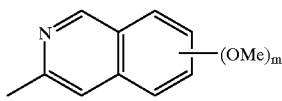

(wherein m is 0 or an integer of 1 to 4), d.

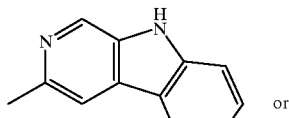

or e.

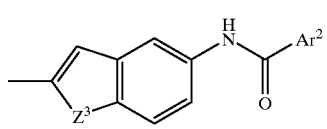

(wherein $Z^3$ is O or NH; $Ar^3$ is any of the above groups of a, b, c, and d), and further relates to protected pyrroloindole derivatives represented by the following general formula (2):

(2)

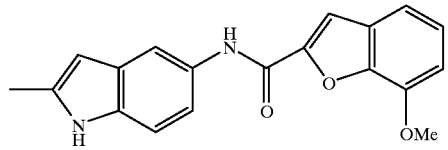

where $R^1$ is $OR^3$ ($R^3$ is a protecting group for the hydroxyl group), n is 1, $R^2$ is methyl, X—Y is O—$CH_2$, $Z^1$ is Cl, and $Ar^1$ is

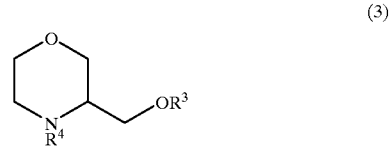

These derivatives are useful as an intermediate for production of the aforementioned carbamoyl group-containing pyrroloindole derivative.

The present invention further relates to an intermediate for production of the aforementioned protected pyrroloindole derivative represented by the following general formula (3), optically active isomers thereof, and salts thereof:

(3)

where $R^3$ is a protecting group for the hydroxyl group, $R^4$ is a hydrogen atom or a benzyl group.

In the general formulas (1) and (2), the lower alkyl group of $C_1$–$C_4$ includes methyl, ethyl, isopropyl, t-butyl, and the like, of which methyl is preferred. The hydroxyl-protecting group represented by $R^3$ includes t-butyldimethylsilyl, triethylsilyl, triisopropylsilyl, t-butyldiphenylsilyl, methoxymethyl, t-butoxymethyl, tetrahydropyranyl, and the like, of which t-butyldimethylsilyl is preferred.

In the present invention, particularly preferred embodiment is represented by the following general formula (4) below:

(4)

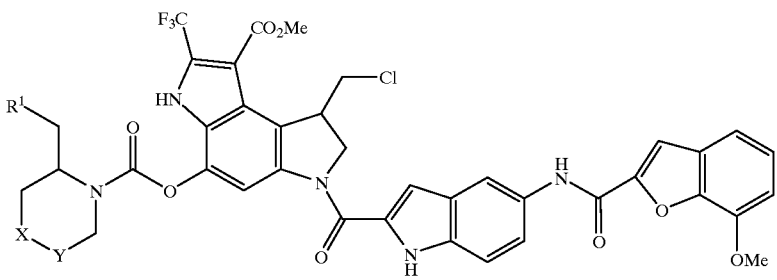

Of the compounds, preferred are the compound in which $R^1$ is pyrrolidinyl, and X—Y is $CH_2$ (Compound I); the compound in which $R_1$ is OH, and X—Y is $CH_2$—$CH_2$ (Compound II); the compound in which $R^1$ is OH, and X—Y or Y—X is O—$CH_2$ (Compound III); and the compound in which $R^1$ is OH, and X—Y or Y—X is NMe—$CH_2$ (Compound IV); and optically active isomers of the above compounds. The compounds I–IV and the optically active isomers thereof may be pharmacologically accepted salts, for example, a hydrochloride salt.

The racemic modifications and optically active isomers of the compounds represented by the general formula (1) can be produced by a known process (e.g., JP-A-6-116269). The compound represented by the general formula (1) may be used alone or in combination with a pharmaceutically acceptable auxiliary agent as an antimicrobial or antitumor composition.

For example, the compound represented by the general formula (1) or the salt thereof is dissolved in physiological saline or an aqueous solution of glucose, mannitol, lactose, or the like for use as a medical composition.

Otherwise, a salt of the compound represented by the general formula (1) is freeze-dried in a conventional manner and mixed with sodium chloride or the like for use as a powdery injectable agent. This medical composition may contain an additive known in medical formulation, for example, a pharmaceutically acceptable salt, as necessary.

The solution-type medical composition can be used as it is. The powdery injectable agent is used after dissolution in distilled water, physiological saline, or an aqueous solution of glucose, mannitol, lactose, or the like for intravenous administration. The medical composition may be administered intra-arterially, intra-abdominally, or intrathoracically, if desired.

The medical composition may be used also for oral administration as tablets, capsules, powders, granules, ampule-medicine, and so forth, and may contain a medical auxiliary agent conventionally employed in medical formulation.

The dosage depends on the age and the symptom of the patient, ranging from 0.00001 to 100 mg/kg/day for mammals including humans. The administration may be conducted once or several times per day, or intermittently one to four times per week, or once in two to four weeks.

BEST MODE FOR CARRYING OUT THE INVENTION

The advantages of the present invention are described below by reference to Test Examples and Working Examples without limiting the invention thereto.

Working Example 1

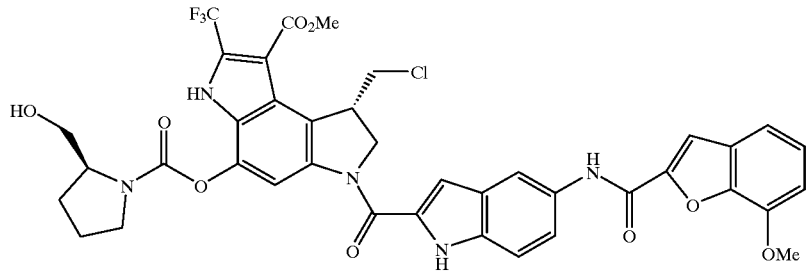

Methyl(1S)-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (10.2 mg, 15 μmol) and 4-nitrophenyl chloroformate (7.6 mg, 38 μmol) were dissolved in 1 mL of tetrahydrofuran, and thereto triethylamine (4.2 μL, 30 μmol) was added dropwise with ice cooling. After one hour, (2S)-pyrrolidine-2-methanol (4.4 μL, 45 μmol) was added dropwise. The mixture was stirred for two hours, and stirred further for two hours at room temperature. The reaction mixture was poured into 3 mL of saturated aqueous sodium chloride solution and 3 mL of ethyl acetate for extraction. The extracted matter was dried over anhydrous sodium sulfate, and the solvent was evaporated off. The resulting residue was purified by silica gel column chromatography (hexane:acetone=1:1) to obtain 8.5 mg (70%) of methyl (1S)-chloromethyl-5-{[(2S)-hydroxymethylpyrrolidin-1-ylcarbonyl]oxy}-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate.

NMR(DMSO-$d_6$) 67 : 1.80–2.10 (4 H,m), 3.30–3.80 (6 H,m), 3.83–4.20 (2 H,m), 3.92 (3 H,s), 4.01 (3 H,s), 4.42 (1 H,brs), 4.60 (1 H,d, J=9.5 Hz), 4.79 (1 H,t, J=9.3 Hz), 7.10 (1 H,dd, J=1.0 Hz,8.1 Hz), 7.21 (1 H,d, J=1.5 Hz), 7.28 (1 H,t, J=7.8 Hz), 7.37 (1 H,dd, J=1.0 Hz,7.8 Hz), 7.50 (1 H,d, J=8.8 Hz), 7.60 (1 H,dd, J=2.0 Hz, 9.0 Hz), 7.75 (1 H,s), 8.17 (1 H,d, J=10.3 Hz), 8.21 (1 H,d, J=1.5 Hz), 10.41 (1 H,s), 11.70 (1 H,s), 13.06 (1 H,brs)

Working Example 2

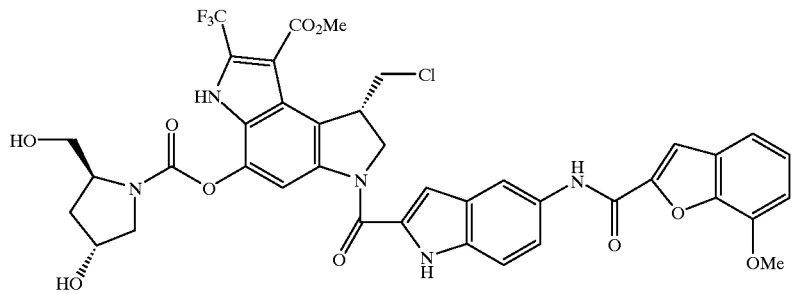

In the same manner as in Working Example 1, methyl (1S)-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (20.4 mg, 30 μmol) and (2S,4R)-4-hydroxypyrrolidin-2-methanol (10.5 mg, 90 μmol) were allowed to react to obtain methyl (1S)-chloromethyl-5-{[(4R)-hydroxy-(2S)-hydroxymethylpyrrolidin-1-ylcarbonyl]oxy}-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (17.3 mg, 70%).

NMR(DMSO-d$_6$) 67 : 1.80–2.20 (2 H,m) , 3.34–3.80 (6 H,m) , 3.90–4.35 (2 H,m), 3.92 (3 H,s), 4.01 (3 H,s), 4.35–4.50 (2 H,m), 4.60 (1 H,d, J=11.2 Hz), 4.75–4.81 (1 H,m), 5.08–5.15 (1 H,m), 7.10 (1 H,d, J=8.3 Hz), 7.21 (1 H,d, J=1.5 Hz), 7.28 (1 H,t, J=7.8 Hz), 7.37 (1 H, d=7.8Hz), 7.50 (1 H,d, J=8.8 Hz), 7.60 (1 H,dd, J=1.5 Hz,8.8 Hz), 7.75 (1 H,s), 8.18–8.30 (2 H,m), 10.41 (1 H,s), 11.71 (1 H,s), 13.09 (1 H,brs)

Working Example 3

In the same manner as in Working Example 1, methyl (1S)-chloromethy-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (20.4 mg, 30 μmol) and (2S)-(pyrrolidin-1-ylmethyl)pyrrolidine (13.9 mg, 90 μmol) were allowed to react to obtain methyl (1S)-chloromethyl-5-{[(2S)-(pyrrolidin-1-ylmethyl)pyrrolidin-1-ylcarbonyl]oxy}-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate. The resulting reaction product was treated with 3M-HCl in methanol(0.5 mL)-ethyl acetate (0.05 mL) to obtain 18.2 mg (68%) of the hydrochloride.

NMR(DMSO-d$_6$) δ: 1.80–2.30 (8 H,m), 2.95–4.05 (10 H,m), 3.91 (3 H,s), 4.00 (3 H,s), 4.28 (1 H,m), 4.41 (1 H,m), 4.61 (1 H,m), 4.80 (1 H,m), 7.10 (1 H,d, J=8.3 Hz), 7.22 (1 H,s), 7.28 (1 H,t, J=7.8 Hz), 7.37 (1 H,d, J=7.8 Hz), 7.51 (1 H,d, J=8.8 Hz), 7.61 (1 H,dd, J=1.5 Hz, 8.8 Hz), 7.76 (1 H,s), 8.19–8.31 (2 H,m), 9.71 (1 H,brs), 10.43 (1 H,s), 11.67 (1 H,s), 13.20 (1 H,brs)

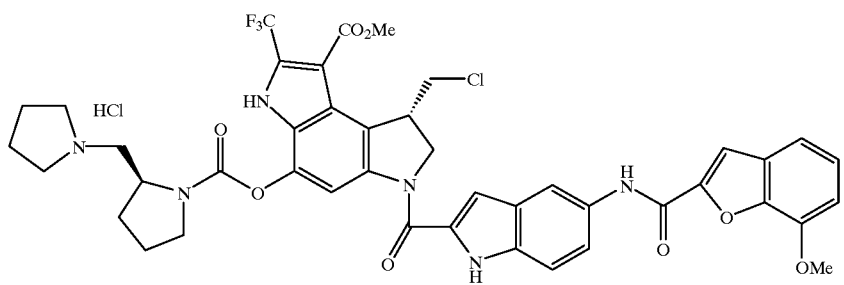

Working Example 4

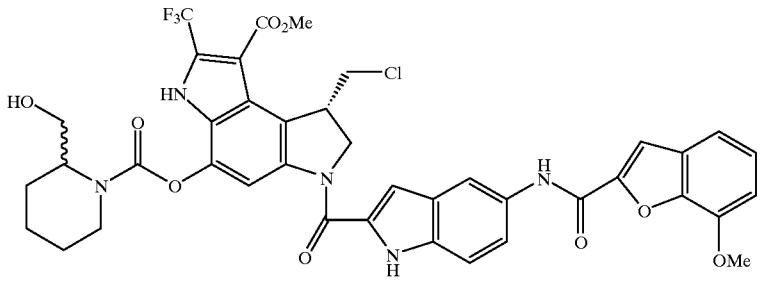

In the same manner as in Working Example 1, methyl (1S)-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (13.6 mg, 20 μmol) and (2RS)-piperidine-2-methanol (6.9 mg, 60 μmol) were allowed to react to obtain methyl (1S)-chloromethyl-5-{[(2RS)-hydroxymethylpiperidin-1-ylcarbonyl]oxy}-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (12.5 mg, 76%).

NMR(DMSO-$d_6$) )δ: 1.40–1.85 (6 H,m), 3.25–3.95 (8 H,m), 3.91 (3 H,s), 4.00 (3 H,s), 4.42 (1 H,m), 4.60 (1 H,d, J=10.7 Hz), 4.80 (1 H,t, J=9.8 Hz), 7.10 (1 H,d, J=8.3 Hz), 7.21 (1 H,s), 7.28 (1 H,t, J=7.8 Hz), 7.36 (1 H,d, J=7.8 Hz), 7.49 (1 H,d, J=8.8 Hz), 7.60 (1 H,dd, J=2.0 Hz, 9.3 Hz), 7.75 (1 H,s), 8.21 (2 H,m), 10.41 (1 H,s), 11.74 (1 H,s)

Working Example 5

In the same manner as in Working Example 3, methyl (1S)-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (27.2 mg, 40 μmol) and (2RS)-4-methylpiperazine-2-methanol (13.0 mg, 100 μmol) were allowed to react and the resulting product was treated to obtain hydrochloride of methyl (1S)-chloromethyl-5-{[(2RS)-hydroxymethyl-4-methylpiperazin-1-ylcarbonyl]oxy}-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (18.8 mg, 54%).

NMR(DMSO-$d_6$) δ: 2.88 (3 H,s) , 3.05–3.95 (10 H,m), 3.92 (3 H,s), 4.00 (3 H,s), 4.14 (1 H,m), 4.20–4.50 (2 H,m), 4.61 (1 H,d, J=11.2 Hz), 4.81 (1 H,t, J=9.3 Hz), 7.10 (1 H,d, J=7.8 Hz), 7.22 (1 H,s), 7.28 (1 H,t, J=7.8 Hz), 7.36 (1 H,d, J=7.8 Hz), 7.50 (1 H,d, J=9.3 Hz), 7.61 (1 H,d, J=10.3 Hz), 7.76 (1 H,s), 8.21–8.31 (2 H,m), 10.00 (1 H,br), 10.43 (1 H,s), 11.66 (1 H,br), 13.11 (1 H,brs)

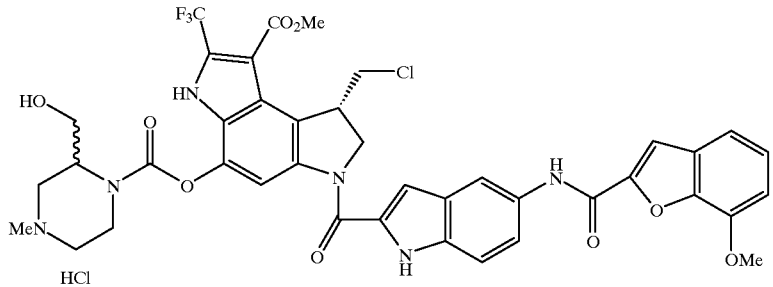

Working Example 6

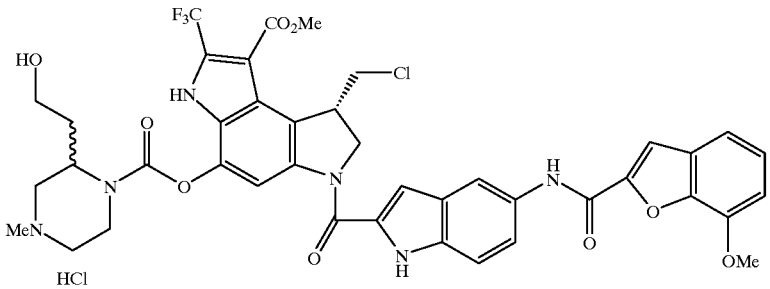

In the same manner as in Working Example 3, methyl (1S)-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (20.4 mg, 30 μmol) and (2RS)-4-methylpiperazine-2-ethanol (12.4 mg, 90 μmol) were allowed to react and the resulting product was treated to obtain hydrochloride of methyl (1S)-chloromethyl-5-{[(2RS)-hydroxyethyl-4-methylpiperazin-1-ylcarbonyl]oxy}-3-[5-(7-methoxybenzofuran-2-ylcarbonyl) amino-1H-indol-2-ylcarbonyl]-7-trifluoromethyl-1,2,3,6-tetrahydropyrrolo[3,2-e]indole-8-carboxylate (16.5 mg, 62%).

NMR(DMSO-$D_6$) )δ: 1.80–2.50 (2 H,m), 2.86 (3 H,s), 3.05–3.95 (10 H,m), 3.92 (3 H,s), 4.00 (3 H,s), 4.08 (1 H,m), 4.43 (1 H,m), 4.59 (1 H,m), 4.80 (1 H,m), 4.94 (1 H,m), 7.10(1 H,d, J=7.8 Hz), 7.22 (1 H,d, J=2.0 Hz), 7.28 (1 H,t, J=7.8 Hz), 7.37 (1 H,dd, J=1.0 Hz, 8.8 Hz), 7.50 (1 H,d, J=8.8 Hz), 7.61 (1 H,dd, J=2.0 Hz, 8.8 Hz), 7.76 (1 H,s), 8.21–8.32 (2 H, m), 10.05 (1 H,brs), 10.43 (1 H,s), 11.67 (1 H,s), 13.17 (1 H,brs)

Working Example 7

In the same manner as in Working Example 1, methyl (1S)-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (20.4 mg, 30 μmol) and (3RS)-morpholine-3-methanol (10.5 mg, 90 μmol) were allowed to react to obtain methyl (1S)-chloromethyl-5-{[(3RS)-hydroxymethylmorpholin-4-ylcarbonyl]o xy}-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (17.5 mg, 71%).

NMR(DMSO-$d_6$) 67 : 3.15–4.05 (11 H,m), 3.92 (3 H,s), 4.00 (3 H,s), 4.29 (1 H,m), 4.43 (1 H,m), 4.61 (1 H,d, J=10.7Hz), 4.80 (1 H,t, J=9.3 Hz), 7.10 (1 H,d,J=7.3 Hz), 7.22 (1 H,d, J=2.0 Hz), 7.28 (1 H,t, J=8.3 Hz), 7.36 (1 H,d, J=7.8 Hz), 7.49 (1 H,d, J=8.8 Hz), 7.60 (1 H,dd, J=2.0 Hz,8.8 Hz), 7.75 (1 H,s), 8.21 (2 H,m), 10.41 (1 H,s), 11.73 (1 H,s), 13.08 (1 H,brs)

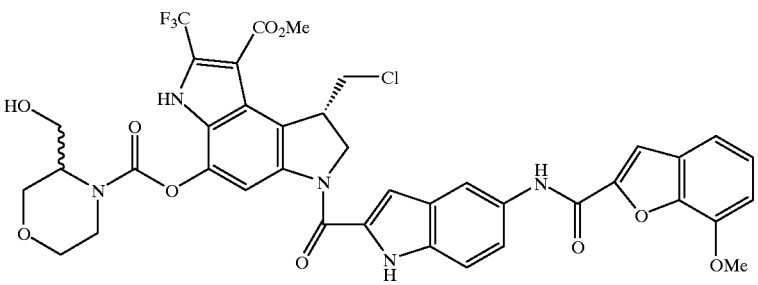

Working Example 8

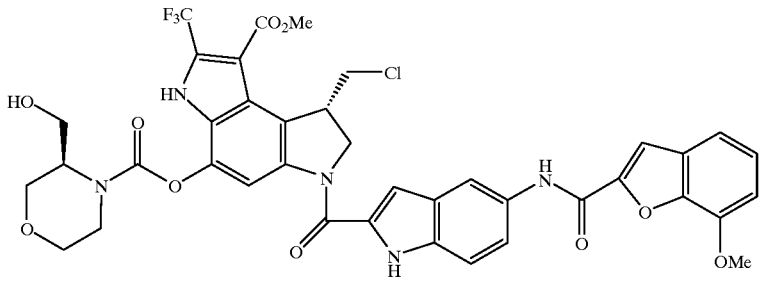

In the same manner as in Working Example 1, methyl (1S)-chloromethyl-5-hydroxy-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (81.7 mg, 0.12 μmol) and (3R)-morpholine-3-methanol (42.2 mg, 0.36 mmol) were allowed to react to obtain methyl (1S)-chloromethyl-5-{[(3R)-hydroxymethylmorpholin-4-ylcarbonyl] oxy}-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (62.9 mg, 64%).

NMR(DMSO-$d_6$) δ: 3.15–4.15 (11 H,m), 3.91 (3 H,s), 4.00 (3 H,s), 4.30 (1 H,m), 4.42 (1 H,m), 4.60 (1 H,d, J=10.7 Hz), 4.80 (1 H,t, J=10.3 Hz), 7.10 (1 H,d, J=7.3 Hz), 7.22 (1 H,s), 7.28 (1 H,t, J=7.8 Hz), 7.37 (1 H,d, J=7.8 Hz), 7.49 (1 H,d, J=8.5 Hz), 7.60 (1 H,dd, J=2.0 Hz, 9.0 Hz), 7.76 (1 H,s), 8.21 (2 H,s), 10.42 (1 H,s), 11.74 (1 H,brs), 12.78, 13.09 (total 1 H,brsx2, in each rotamer)

In the same manner as in Working Example 1, methyl (1S)-chloromethyl-5-hydroxy-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (81.7 mg, 0.12 mmol) and (3S)-morpholine-3-methanol (42.2 mg, 0.36 mmol) were allowed to react to obtain methyl (1S)-chloromethyl-5-{[(3S)-hydroxymethylmorpholin-4-ylcarbonyl] oxy}-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (69.7 mg, 70%).

NMR(DMSO-$d_6$) δ: 3.10–4.15 (11 H,m), 3.91 (3 H,s), 4.00 (3 H,s), 4.28 (1 H,m), 4.43 (1 H,m), 4.60 (1 H,d, J=11.0 Hz), 4.80 (1 H,t, J=10.5 Hz), 7.10 (1 H,d, J=7.3 Hz), 7.23 (1 H,d, J=2.0 Hz), 7.28 (1 H,t, J=7.8 Hz), 7.37 (1 H,d, J=7.8 Hz), 7.49 (1 H,d, J=9.0 Hz), 7.60 (1 H,dd, J=2.0 Hz, 8.8 Hz), 7.76 (1 H,s), 8.21 (2 H,m), 10.42 (1 H,s), 11.73 (1 H,s), 12.85, 13.11 (total 1 H,brsx2, in each rotamer).

Working Example 9

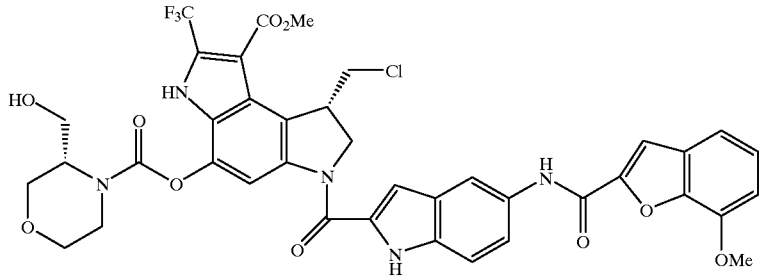

Working Example 10

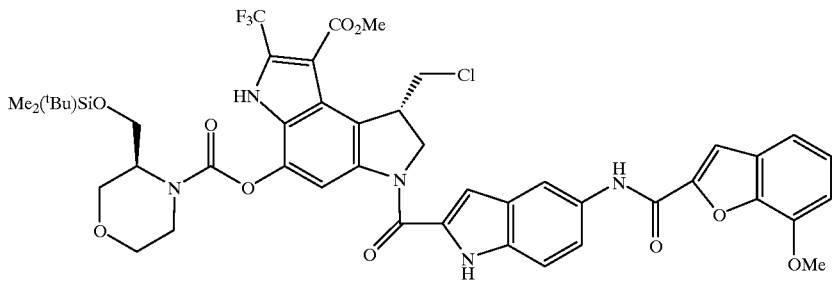

Methyl(1S)-chloromethyl-5-hydroxy-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (1.02 g, 1.5 mmol) and 4-nitrophenyl chloroformate (0.51 g, 2.55 mmol) were dissolved in 50 mL of tetrahydrofuran, and thereto triethylamine (313.6 μL, 2.25 mmol) was added dropwise with ice cooling. After 1.5 hours, (3S)-3-(t-butyldimethylsilyloxy)-methylmorpholine hydrochloride (0.80 g, 3.0 mmol) and triethylamine (0.52 mL, 3.75 mmol) were added thereto. The mixture was stirred overnight. The reaction mixture was diluted with 50 mL of ethyl acetate, washed with saturated aqueous sodium chloride solution, and dried over anhydrous sodium sulfate. After the solvent was evaporated off, the resulting residue was purified by silica gel column chromatography (hexane:ethyl accetate=1:1) to obtain methyl (1S)-chloromethyl-5-{[(3S)-(t-butyldimethylsilyloxy)-methylmorpholin-4-ylcarbonyl]oxy}-3-[5-[7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (1.08 g, 77%).

NMR(DMSO-$d_6$) )δ: 0.04,0.07 (total 6 H,sx2, in each rotamer), 0.85,0.86 (total 9H,sx2, in each rotamer), 3.15–4.10 (10 H,m), 3.91 (3 H,s), 4.00 (3 H,s), 4.19 (1 H,m), 4.40 (1 H,m), 4.59 (1 H,d, J=11.2 Hz), 4.80 (1 H,t, J=10.7 Hz), 7.10 (1 H,d, J=7.8 Hz), 7.22 (1 H,s), 7.28 (1 H,t, J=8.1 Hz), 7.37 (1 H,d, J=7.6 Hz), 7.50 (1 H,d, J=8.8 Hz), 7.60 (1 H,dd, J=2.0 Hz,9.0 Hz), 7.76 (1 H,s), 8.17 (2 H,m), 10.42 (1 H,s), 11.69 (1 H,s), 13.09 (1 H,brs)

Working Example 11

In the same manner as in Working Example 10, methyl (1S)-chloromethyl-5-hydroxy-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (1.36 g, 2.0 mmol) and (3R)-3-(t-butyldimethylsilyloxy)-methylmorpholine hydrochloride (1.07 g, 4.0 mmol) were allowed to react to obtain methyl (1S)-chloromethyl-5-{[(3R)-(t-butyldimethylsilyloxy)-methylmorpholin-4-ylcarbonyl]oxy]-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (1.58 g, 84%).

NMR (DMSO-$d_6$) δ: 0.07,0.08 (total 6 H,sx2, in each rotamer), 0.867,0.874 (total 9 H,sx2, in each rotamer), 3.15–4.10 (10 H,m), 3.91 (3 H,s), 4.00 (3 H,s), 4.21 (1 H,m), 4.41 (1 H,m), 4.59 (1 H,d,J=10.5 Hz), 4.80 (1 H,t,J=10.2 Hz), 7.10 (1 H,d,J=7.6 Hz), 7.22 (1 H,s), 7.28 (1 H,t,J=7.8 Hz), 7.37 (1 H,d,J=7.8 Hz), 7.50 (1 H,d,J=8.8 Hz), 7.60 (1 H,dd,J=2.0 Hz,8.8 Hz), 7.76 (1 H,s), 8.18 (1 H,s), 8.20 (1 H,s), 10.42 (1 H,s), 11.69 (1 H,s), 13.08 (1 H,brs)

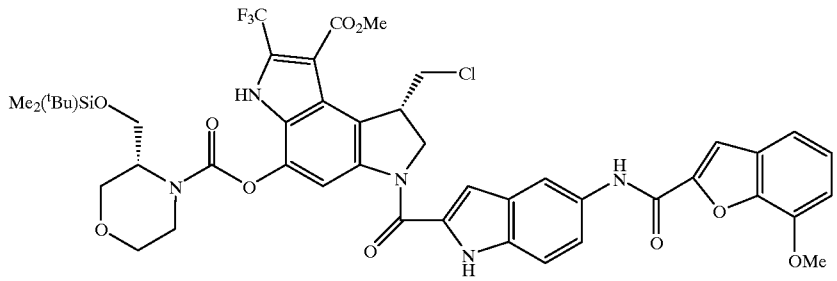

Working Example 12

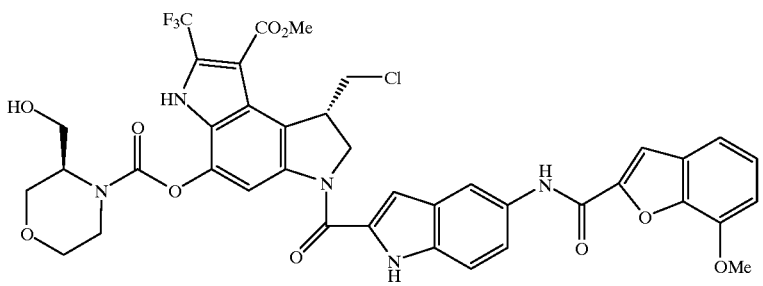

Methyl(1S)-chloromethyl-5-[(3S)-(t-butyldimethylsilyloxy)methylmorpholin-4-ylcarbonyl)oxy]-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (1.03 g, 1.1 mmol) was suspended in 2 mL of ethyl acetate and 8 mL of isopropanol. Thereto, 5.5 mL of 1 N hydrochloric acid in isopropyl alcohol was added, and the mixture was stirred at room temperature for one hour. The reaction mixture was cooled by ice. Thereto, 10 mL of isopropyl ether was added and the mixture was stirred for 15 minutes. The formed crystalline matter was collected by filtration, and washed with isopropyl ether to obtain methyl (1S)-chloromethyl-5-{[(3R)-hydroxymethylmorpholin-4-ylcarbonyl]oxy}-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (0.83 g, 92%) as colorless crystals. This substance is the same as the one obtained in Working Example 8.

Working Example 13

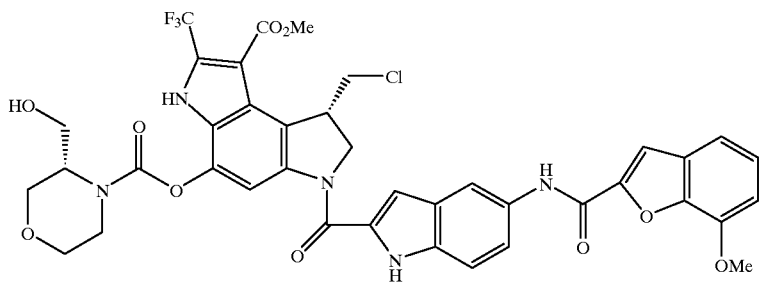

In the same manner as in Working Example 12, methyl (1S)-chloromethyl-5-{[(3R)-(t-butyldimethylsilyloxy)-methylmorpholin-4-ylcarbonyl]oxy}-3-[5-[(7-methoxybenzofuran-2-ylcarbonyl)amino]-1H-indol-2-ylcarbonyl]-7-trifluoromethyl-1,2,3,6-tetrahydropyrrolo[3,2-e]indole-8-carboxylate (1.41 g, 1.5 mmol) was treated to obtain methyl (1S)-chloromethyl-5-{[(3S)-hydroxymethylmorpholin-4-ylcarbonyl] oxy}-3-[5-(7-methoxybenzofuran-2-ylcarbonyl)amino-1H-indol-2-ylcarbonyl]-7-trifluoromethyl-1,2,3,6-tetrahydropyrrolo[3,2-e]indole-8-carboxylate (1.20 g, 97%) as colorless crystals. This substance is the same as the one obtained in Working Example 9.

Working Example 14

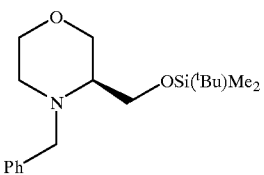

(3R)-4-Benzylmorpholine-3-methanol (1.04 g, 5.0 mmol), t-butyldimethylchlorosilane (0.83 g, 5.5 mol), and imidazole (0.41 g, 6.0 mmol) were allowed to react in 5 mL of dichloromethane at room temperature overnight. The reaction product was purified by silica gel column chromatography (hexane:ethyl acetate=5:1) to obtain (3S)-3-(t-butyldimethylsilyloxy)methyl-4-benzylmorpholine (1.53 g, 95%) as a colorless oil.

Working Example 15

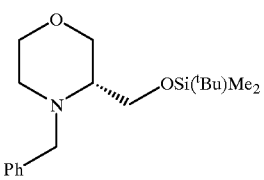

In the same manner as in Working Example 14, (3S)-4-benzylmorpholine-3-methanol (1.24 g, 6.0 mmol) was treated to obtain (3R)-3-(t-butyldimethylsilyloxy)methyl-4-benzylmorpholine (1.82 g, 94%) as a colorless oil.

Working Example 16

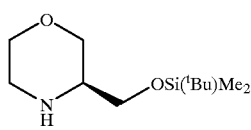

(3R)-Morpholine-3-methanol (84.8 mg, 0.72 mmol), t-butyldimethylchlorosilane (0.11 g, 0.72 mmol), and imidazole (59.1 mg, 0.87 mmol) were allowed to react in 1 mL of dichloromethane at room temperature for 2 hours. The reaction product was purified by silica gel chromatography (dichloromethane:methanol:acetone=15:1:0.5) to obtain (3S)-3-(t-butyldimethylsilyloxy)methylmorpholine (0.15 g, 92%) as a colorless oil.

Working Example 17

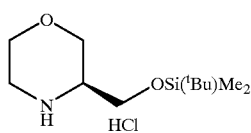

(3S)-3-(t-Butyldimethylsilyloxy)methyl-4-benzylmorpholine (1.19 g, 3.7 mmol) was treated for hydrogenation in the presence of 10% palladium-carbon (0.36 g) in 5 mL of ethanol and 0.32 mL of chloroform for 4 hours (one atmosphere). The catalyst was removed by filtration, and the filtrate was concentrated. The precipitated crystalline matter was washed with ether to obtain (3S)-3-(t-butyldimethylsilyloxy)methylmorpholine hydrochloride (0.96 g (96%).

Working Example 18

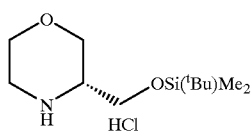

In the same manner as in working Example 17, (3R)-3-(t-butyldimethylsilyloxy)methyl-4-benzylmorpholine (1.82 g, 5.6 mmol) was treated to obtain (3R)-3-(t-butyldimethylsilyloxy)methylmorpholine hydrochloride (1.13 g, 74%).

Test Example 1

Decomposition reaction under chemical conditions:

A buffer solution of pH 7.4 was prepared by mixing suitably an aqueous 0.1 M citric acid solution and an aqueous 0.2 M disodium hydrogenphosphate solution. The buffer solution was diluted tenfold with water. This buffer solution was further dissolved in N,N-dimethylacetamide at a concentration of 50 v/v%, and its pH was adjusted to 7.4 by adding suitable amount of aqueous 0.1 M citric acid solution to prepare a buffer solution. The test compounds were dissolved respectively in the buffer solution at a concentration of 5 µM to prepare the test sample solutions. The test sample solutions were placed respectively in a glass vial, and the glass vials were kept at 37° C. in a thermostat. The change of the concentration of remaining test compounds with lapse of time was determined quantitatively intermittently by high performance liquid chromatography (HPLC) to measure the half life ($t_{1/2}$: hours). Table 1 shows the test results.

TABLE 1

| Test compound | Half life ($t_{1/2}$: hours) | Test compound | Half life ($t_{1/2}$: hours) |
|---|---|---|---|
| Example 1 | >8 | Example 5 | 1.7* |
| Example 2 | >8 | Example 6 | 5.8* |
| Example 3 | 1.0 | Example 7 | 1.7* |
| Example 4 | >8* | | |

*Average of the half lives of the diastereomers

The compounds of the present invention decomposes rapidly in the buffer solution of pH 7.4 to form the active species.

Test Example 2

Evaluation with mouse bearing M5076/ADR cells (adriamycin-resistant strain) transplanted subcutaneously:

M5076/ADR cells (adriamycin-resistant strain) were transplanted subcutaneously at the axillary region of female mice (BDFI strain, 8 week age) in an amount of $3.0 \times 10^6$ cells for an individual mouse. Nine days after the transplantation, the test compound solution was injected once into the tail vein. After 13 days from the injection, the tumor was excised and weighed. The antitumor activity was evaluated by the ratio (T/C) of the average tumor weight (T) of the administrated group to the average tumor weight (C) of control group to which solvent was administrated. Table 2 shows the effects.

TABLE 2

| Test compound | Dose (mg/kg) | T/C |
|---|---|---|
| Example 4 | 1.0 | 0.01 |
| Example 5 | 1.0 | 0.01 |
| Example 6 | 1.0 | 0.02 |

The compounds of the present invention showed excellent antitumor effect against M5076/ADR cells (adriamycin-resistant strain).

INDUSTRIAL APPLICABILITY

The pyrroloindole derivative of the present invention, which has a carbamoyloxy group comprising a cyclic amine having hydroxyalkyl or pyrrolidinylalkyl at α-position to the nitrogen of the carbamoyl group, decomposes at an appropriate rate in vivo or under chemical conditions to produce active species, although carbamoyl groups comprising a cyclic amine are generally st able. Such a prodrug have firstly produced according to the present invention. The prodrug compounds of the present invention are effective against solid tumor, and are less toxic and exhibit antitumor activity in a broad safety range. Therefore the chemotherapy for patients with cancer can be conducted with less adverse effects.

What is claimed is:

1. A pyrroloindole derivative having a carbamoyloxy group represented by the following general formula (1) below, an optically active isomer thereof, and a pharmacologically acceptable salt thereof:

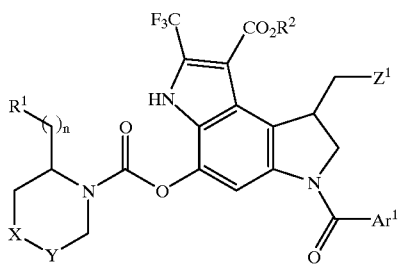

where R¹ is OH, or a pyrrolidinyl group; n is 1 or 2; R² is a lower alkyl group of $C_1$–$C_4$; X—Y or Y—X is $CH_2$, CHOH, $CH_2$–$CH_2$, O—$CH_2$, or NMe—$CH_2$; $Z^1$ is Cl or Br; and Ar¹ is a.

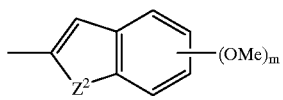

wherein $Z^2$ is O or NH, m is 0 or an integer of 1 to 4, b.

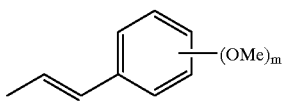

wherein m is 0 or an integer of 1 to 4, c.

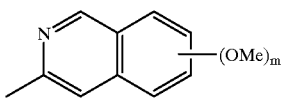

wherein m is 0 or an integer of 1 to 4, d.

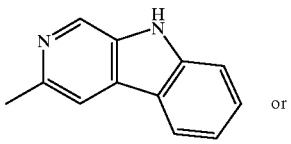

or e.

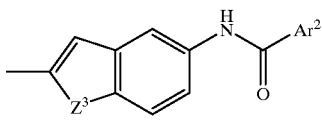

wherein $Z^3$ is O or NH; Ar² is any of the above groups a, b, c, and d.

2. The pyrroloindole derivative having a carbamoyloxy group according to claim 1 represented by the following general formula (1) below, the optically active isomer thereof, and the pharmacologically acceptable salt thereof:

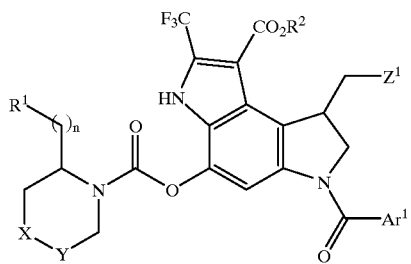

where R¹ is a pyrrolidinyl group, n is 1, R² is methyl, X—Y is $CH_2$, $Z^1$ is Cl, and Ar¹ is

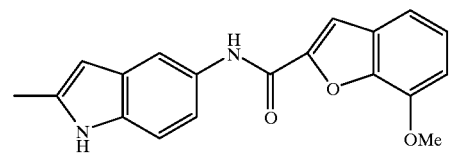

3. The pyrroloindole derivative having a carbamoyloxy group according to claim 1 represented by the following general formula (1) below, and the optically active isomer thereof:

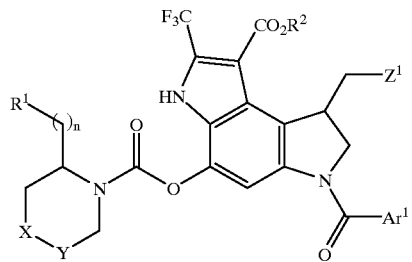

where R¹ is OH, n is 1, R² is methyl, X—Y is $CH_2$–$CH_2$, $Z^1$ is Cl, and Ar¹ is

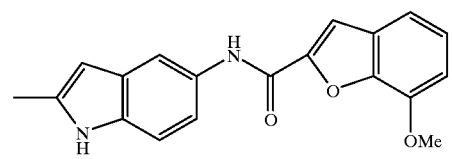

4. The pyrroloindole derivative having a carbamoyloxy group according to claim 1 represented by the following general formula (1) below and the optically active isomer thereof:

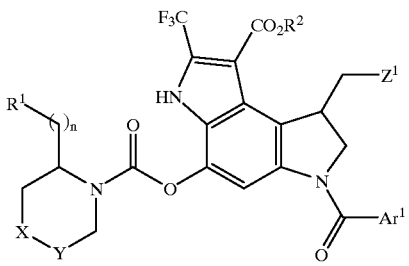

(1)

where R¹ is OH, n is 1, R² is methyl, X—Y or Y—X is O—CH₂, Z¹ is

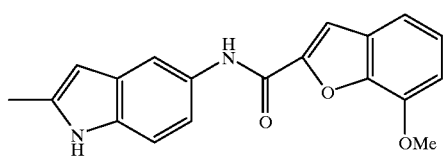

5. The pyrroloindole derivative having a carbamoyloxy group according to claim 1 represented by the following general formula (1) below, the optically active isomer thereof, and the pharmacologically acceptable salt thereof:

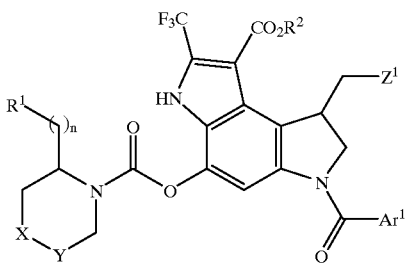

(1)

where R¹ is OH, n is 1, R² is methyl, X—Y or Y—X is NMe—CH₂, Z¹ is Cl, and Ar¹ is

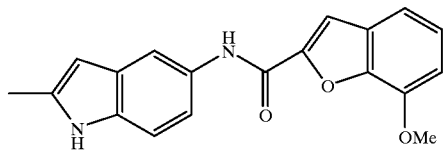

6. A protected pyrroloindole derivative represented by the following general formula (2):

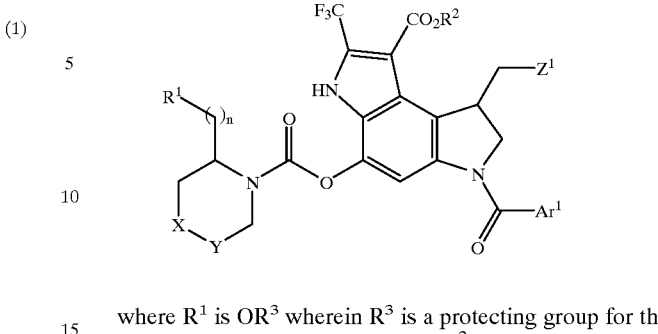

(2)

where R¹ is OR³ wherein R³ is a protecting group for the hydroxyl group; n is 1 or 2; R² is a lower alkyl of $C_1$–$C_4$; X—Y is CH₂, CHOH, CH₂–CH₂, O—CH₂, or NMe—CH₂; Z¹ is Cl or Br; and Ar¹ is a.

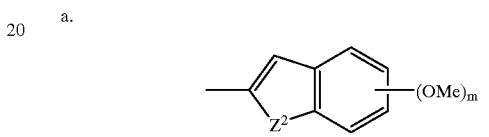

wherein Z² is O or NH, m is 0 or an integer of 1 to 4, b.

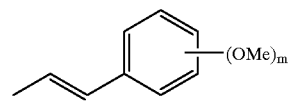

wherein m is 0 or an integer of 1 to 4, c.

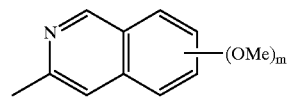

wherein m is 0 or an integer of 1 to 4, d.

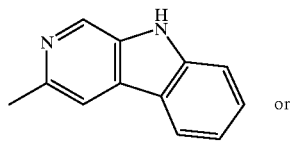

or e.

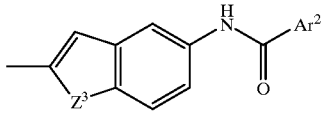

wherein Z³ is O or NH; Ar² is any of the above groups of a, b, c, and d).

7. The protected pyrroloindole derivative according to claim 6 represented by the following general formula (2):

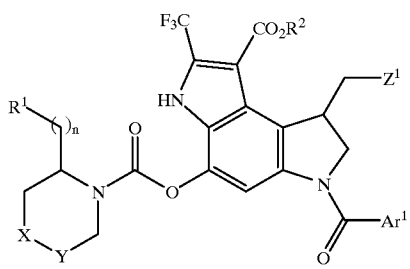
(2)
where $R^1$ is $OR^3$ wherein $R^3$ is a protecting group for the hydroxyl group, n is 1, $R^2$ is methyl, X—Y is O—CH$_2$, $Z^1$ is Cl, and $Ar^1$ is
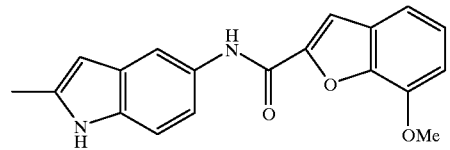
* * * * *

UNITED STATES PATENT AND TRADEMARK OFFICE
CERTIFICATE OF CORRECTION

PATENT NO.     : 6,080,859
DATED          : June 27, 2000
INVENTOR(S)    : Yasumichi Fukuda et al.

It is certified that error appears in the above-identified patent and that said Letters Patent is hereby corrected as shown below:

<u>Title page,</u>
Item [73], Assignee, should read -- Kyorin Pharmaceutical Co., Ltd., Tokyo, Japan and Sagami Chemical Research Center, Kanagawa, Japan --

Signed and Sealed this

Tenth Day of May, 2005

JON W. DUDAS
*Director of the United States Patent and Trademark Office*

REEXAMINATION CERTIFICATE (4722nd)
United States Patent
Fukuda et al.

(10) Number: US 6,080,859 C1
(45) Certificate Issued: Jan. 14, 2003

(54) PYRROLOINDOLE DERIVATIVES AND INTERMEDIATES IN PRODUCING THE SAME

(75) Inventors: Yasumichi Fukuda, Tochigi (JP); Rumiko Shimazawa, Tokyo (JP); Yasuo Oomori, Tokyo (JP); Shiro Terashima, Tokyo (JP)

(73) Assignees: Kyorin Pharmaceutical Co., Ltd., Tokyo (JP); Sagami Chemical Research Center, Sagamihara (JP)

Reexamination Request:
No. 90/006,179, Jan. 7, 2002

Reexamination Certificate for:
Patent No.: 6,080,859
Issued: Jun. 27, 2000
Appl. No.: 09/341,872
Filed: Jul. 19, 1999

(22) PCT Filed: Jan. 22, 1998
(86) PCT No.: PCT/JP98/00234
§ 371 (c)(1), (2), (4) Date: Jul. 19, 1999
(87) PCT Pub. No.: WO98/32757
PCT Pub. Date: Jul. 30, 1998

(30) Foreign Application Priority Data

Jan. 24, 1997 (JP) .............................................. 9-011289

(51) Int. Cl.[7] .................. A61K 31/5377; C07D 413/14
(52) U.S. Cl. .......................... 544/143; 544/69; 544/142; 544/373; 546/199; 548/433; 514/235.2
(58) Field of Search .......................... 544/143; 546/199; 548/433

(56) References Cited

FOREIGN PATENT DOCUMENTS

| | | |
|---|---|---|
| EP | 0406749 A1 | 1/1991 |
| EP | 0499130 A1 | 8/1992 |
| EP | 0520435 A2 | 12/1992 |
| EP | 0537575 A1 | 4/1993 |
| EP | 0656360 A1 | 6/1995 |

*Primary Examiner*—Laura L. Stockton

(57) ABSTRACT

Pyrroloindole derivatives having antimicrobial and antitumor activities and having a carbamoyloxy group represented by the following general formula (1), optical isomers thereof, and pharmacologically acceptable salts thereof; and intermediates for production thereof:

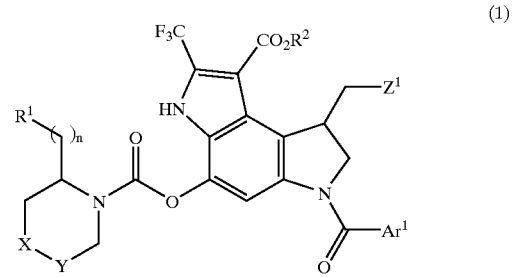

where $R^1$ is OH, or a pyrrolidinyl group; n is 1 or 2; $R^2$ is a lower alkyl group of $C_1$–$C_4$; X—Y or Y—X is $CH_2$, CHOH, $CH_2$—$CH_2$, O—$CH_2$, or NMe—$CH_2$; $Z^1$ is Cl or Br; and $Ar^1$ is a.
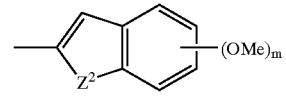

b.
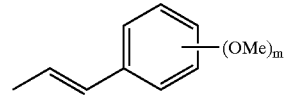

c.
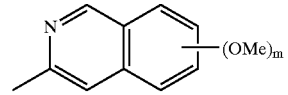

d.

e.
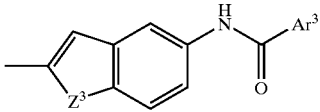

wherein $Z^2$ and $Z^3$ are O or NH; m is 0 or an integer of 1 to 4; and $Ar^2$ is any of the above groups a, b, c, and d.

REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–3 and 5–7 is confirmed.

Claim 4 is determined to be patentable as amended.

4. The pyrroloindole derivative having a carbamoyloxy group according to claim 1 represented by the following general formula (1) below and the optically active isomer thereof:

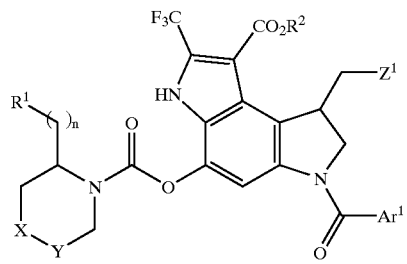

where $R^1$ is OH, n is 1, $R^2$ is methyl, X—Y or Y—X is O-$CH_2$, $Z^1$ is *Cl and $Ar^1$ is*

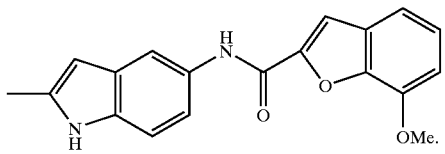

* * * * *